United States Patent
Taylor

(10) Patent No.: US 10,605,642 B1
(45) Date of Patent: Mar. 31, 2020

(54) CONDUCTIVE LIQUID SENSING SYSTEM

(71) Applicant: Altec Industries, Inc., Birmingham, AL (US)

(72) Inventor: John Taylor, Thornton, CO (US)

(73) Assignee: Altec Industries, Inc., Birmingham, AL (US)

( * ) Notice: Subject to any disclaimer, the term of this patent is extended or adjusted under 35 U.S.C. 154(b) by 0 days.

(21) Appl. No.: 16/697,609

(22) Filed: Nov. 27, 2019

(51) Int. Cl.
*G01F 23/24* (2006.01)
*G01N 27/07* (2006.01)
*G01N 27/04* (2006.01)

(52) U.S. Cl.
CPC ......... *G01F 23/241* (2013.01); *G01N 27/045* (2013.01); *G01N 27/07* (2013.01)

(58) Field of Classification Search
USPC ........................................................ 73/304 R
See application file for complete search history.

(56) References Cited

U.S. PATENT DOCUMENTS

| | | | | |
|---|---|---|---|---|
| 3,878,369 A | * | 4/1975 | Gahwiler | G01N 15/1227 377/12 |
| 3,919,627 A | * | 11/1975 | Allen | G01N 27/06 324/443 |
| 4,132,944 A | * | 1/1979 | Bentz | G01N 27/02 324/441 |
| 4,656,427 A | * | 4/1987 | Dauphinee | G01N 27/07 204/400 |
| 4,692,752 A | | 9/1987 | Abel | |
| 4,823,087 A | * | 4/1989 | Sugimori | G01N 27/046 324/439 |
| 4,833,413 A | * | 5/1989 | Head | G01N 27/06 324/444 |
| 5,059,902 A | * | 10/1991 | Linder | G01B 7/023 324/204 |
| 5,260,663 A | * | 11/1993 | Blades | G01R 27/22 204/402 |
| 5,519,323 A | * | 5/1996 | Kordas | G01N 27/06 257/532 |
| 5,543,717 A | * | 8/1996 | Kordas | G01N 27/06 324/439 |
| 5,764,048 A | * | 6/1998 | Yoshida | G01R 1/28 324/120 |
| 8,470,162 B2 | * | 6/2013 | Miyazaki | G01N 33/48771 205/777.5 |
| 8,521,442 B2 | * | 8/2013 | Wang | G01R 27/22 324/439 |
| 2003/0051557 A1 | * | 3/2003 | Ishikawa | G01F 1/588 73/861.12 |
| 2005/0276133 A1 | * | 12/2005 | Harding | G01N 33/48785 365/203 |

(Continued)

*Primary Examiner* — Nathaniel T Woodward
(74) *Attorney, Agent, or Firm* — Erise IP, P.A.

(57) ABSTRACT

Embodiments of the invention provide for a conductive liquid detection system. In some embodiments, the conductive liquid detection system comprises electrodes disposed in a vessel including the conductive liquid. When the conductive liquid contacts the electrodes a signal is passed from an output to an input of a processor through the conductive liquid. In some embodiments, alternative digital high and digital low are passed to eliminate asymmetry effects between the electrodes. In some embodiments, the current is reversed to control electrolysis of the electrodes.

20 Claims, 5 Drawing Sheets

(56) References Cited

U.S. PATENT DOCUMENTS

| | | | | |
|---|---|---|---|---|
| 2009/0014329 A1* | 1/2009 | Silveri | ............... | G01N 27/4168 |
| | | | | 204/412 |
| 2014/0152332 A1* | 6/2014 | Platte | .................... | G01N 27/06 |
| | | | | 324/713 |
| 2016/0097662 A1* | 4/2016 | Chang | ....................... | G01F 1/60 |
| | | | | 73/861.12 |
| 2018/0321181 A1* | 11/2018 | Holmstrom | ........ | A61B 5/14542 |
| 2020/0018627 A1* | 1/2020 | Arai | ........................ | G01F 1/588 |

* cited by examiner

CONDUCTIVE LIQUID SENSING SYSTEM

BACKGROUND

1. Field

Embodiments of the invention are broadly directed to sensing liquid levels. More specifically, embodiments of the invention are directed to detecting conductive liquid levels with electric sensors.

2. Related Art

Typically, electrical liquid level detection systems use electrodes disposed in a tank. When a liquid contacts the electrodes, the liquid conducts a current from one electrode to another completing a circuit. These liquid detection systems have several drawbacks. As current is passed between the electrodes, electrolysis occurs. Electrolysis causes electrode corrosion and may further interrupt the electrical connection between the electrodes. The electrode corrosion results in a short life span of the electrodes and the circuit. Consequently, the electrodes need continual replacement. Further, typical detectors do not compensate for asymmetries in the electrodes causing small direct current to flow between the electrodes. Ignoring this current flow can potentially lead to the detector reporting a false-positive. Further, these typical systems do not have accurate readings. Therefore, system characteristics such as liquid conductivity and liquid resistance cannot be accurately determined.

What is needed is a conductive liquid sensing system that negates electrolysis, cancels the effects of asymmetry, and filters noise. In some embodiments, this is achieved by providing a circuit with electrodes disposed in a tank. The electrodes may have a supplied electrical power such that when the conductive liquid is in contact with the electrodes, the circuit is completed. A voltage measurement may be taken when the power supply provides a high supply and a second voltage measurement taken when the power supply provides a low. The effects of asymmetry and common mode noise may be cancelled by taking a difference between the first voltage measurement and the second voltage measurement. The resulting voltage may provide a value without the effects of asymmetry as well as common-mode noise. Further, the circuit may alternate between power out and power in to negate the effects of electrolysis. In some embodiments, filters may be applied to further reduce noise. The combination of the configurations and processes described herein present an accurate and efficient conductive liquid detection system.

SUMMARY

Embodiments of the invention solve these problems by providing a system and method of detecting a conductive liquid by measuring a voltage across two electrodes disposed in the conductive liquid. In particular, in a first embodiment, the invention includes a method of detecting a conductive liquid with electrodes of a circuit disposed in the conductive liquid, the method comprising the steps of applying a first digital high at a first digital output of a microprocessor, wherein the first digital high is connected to a first electrode by a first switch, measuring a first voltage at a first analog input of the microprocessor, wherein the first analog input is connected to a second electrode by a second switch, applying a first digital low at the first digital output, measuring a second voltage at the first analog input, determining a first final voltage by calculating a difference between the first voltage and the second voltage, switching the first switch to connect a second analog input to the first electrode, switching the second switch to connect a second digital output to the second electrode, applying a second digital high at the second digital output, measuring a third voltage at the second analog input, applying a second digital low at the second digital output, measuring a fourth voltage at the second analog input, determining a second final voltage by calculating a difference between the third voltage measurement and the fourth voltage measurement, and determining a final voltage by averaging the first final voltage and the second final voltage, wherein the final voltage is indicative of the first electrode and the second electrode contacting the conductive liquid.

A second embodiment is directed to a system of detecting a conductive liquid using electrodes in contact with the conductive liquid comprising a circuit for transmitting electrical signals between a output and an input, the circuit comprising a first electrode and a second electrode separately disposed in the conductive liquid, and a microprocessor including a digital output selectively attached to the first electrode and an analog input selectively attached to the second electrode, wherein a digital high is applied at the first digital output, wherein a digital low is applied at the first digital output, and one or more non-transitory computer-readable media storing computer-executable instructions that, when executed by a processor, perform a method of detecting the conductive liquid, the method comprising the steps of measuring a first voltage at the analog input when the digital high is applied at the digital output, measuring a second voltage at the analog input when the digital low is applied at the digital output, determining a first final voltage by calculating a difference between the first voltage and the second voltage, wherein the first final voltage is indicative of the first electrode and the second electrode in contact with the conductive liquid.

A third embodiment is directed to a method of detecting a conductive liquid with electrodes of a circuit disposed in the conductive liquid, the method comprising the steps of applying a first electrical power at a first digital output connected to a first electrode by a first switch, measuring a first voltage at a first analog input connected to a second electrode by a second switch, applying a second electrical power at the first digital output, measuring a second voltage at the first analog input, applying the first electrical power at a second digital output connected to the second electrode by the second switch, measuring a third voltage at a second analog input connected to the first electrode by the first switch, applying the second electrical power at the second digital output, measuring a fourth voltage at the second analog input, determining a first final voltage by calculating a difference between the first voltage and the second voltage, wherein calculating the difference between the first voltage and the second voltage cancels a first asymmetry effect between the first electrode and the second electrode, determining a second final voltage by calculating a difference between the third voltage and the fourth voltage, wherein calculating the difference between the third voltage and the fourth voltage cancels a second asymmetry effect between the first electrode and the second electrode, and determining a final voltage by averaging the first final voltage and the second final voltage.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF DRAWINGS

Embodiments of the invention are described in detail below with reference to the attached drawing figures, wherein.

Figure 1:
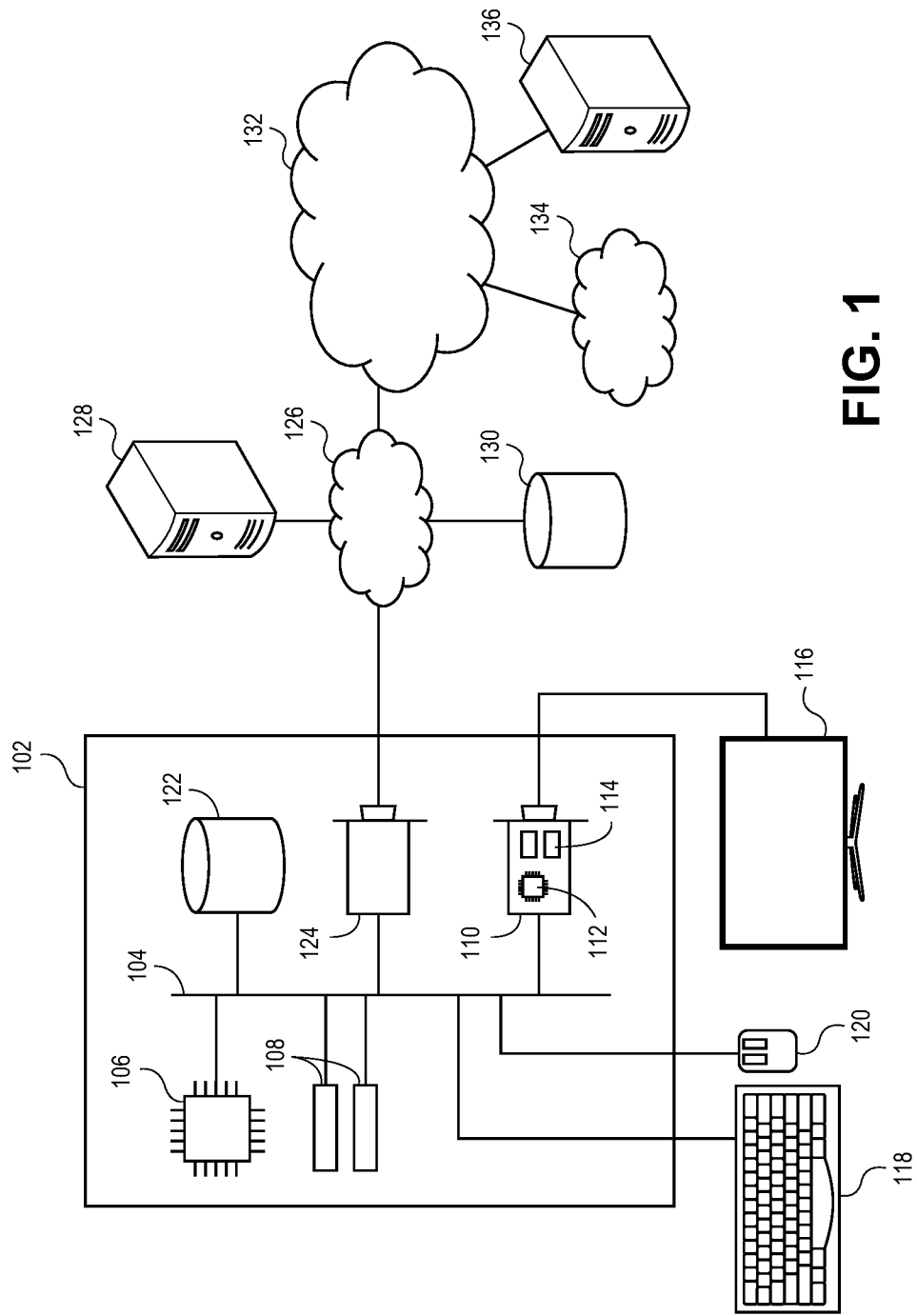
FIG. 1 depicts an exemplary embodiment of hardware for use in embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized, and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Generally, embodiments described herein are presented in a four-part process for determining a final voltage that is indicative of the electrodes in contact with a conductive liquid. The final voltage may be a combination of measured and calculated voltages across a circuit in different configurations. As the conductive liquid conducts electricity from a first electrode to a second electrode, in some embodiments, the conductive liquid is treated as a component of the circuit.

The first part of the four-part process is supplying electrical power to a first electrode. In some embodiments, the power may be supplied as a digital high or a digital low. The digital high may be a five-volt supply or in the range of four to six volts. The digital low may be in the range of zero to 1 volts. The voltage at an analog input connected to a second electrode is then measured. The measurement will indicate a voltage if the first electrode and the second electrode are in contact with the conductive liquid.

The second part of the four-part process is supplying a digital low to the first electrode and measuring the voltage at the analog input. In some embodiments, a first final voltage is determined by subtracting the first voltage and the second voltage. This process may cancel asymmetry effects and common-mode noise.

The third and fourth parts of the four-part process are the same as the first and second parts except the circuit is switch. The power is supplied at the second electrode and the voltage is measured at an analog input associated with the first electrode. In the third part, digital high is supplied and the first measurement is taken. In the fourth part, digital low is supplied and the second voltage measurement is taken. Again, the second final voltage is determined by subtracting the voltage measurements to cancel the asymmetry voltage and the common-mode noise. The first final voltage and the second final voltage may then be averaged to determine a final voltage. This final voltage may be indicative of the conductive liquid resistance. Using the four-part process generally described above reduces degradation of electrodes, common-mode noise, and asymmetry effects in the system.

In some embodiments, electrodes are disposed in the conductive liquid to pass current through the conducting liquid. The electrodes may corrode from electrolysis and the electrodes may have different conductivities or asymmetries between them. These differences may result in a small direct current other than the provided current flowing between the electrodes. This small current is generally referred to herein as the asymmetry effect. The asymmetry effect voltage that induces the asymmetry effect current is typically small. Even this small amount of voltage is enough to confuse typical detections systems. This asymmetry effect may also result in noise in the system. Embodiments described below provide a circuit that cancels the asymmetry effect and any inherent, or common mode, noise in the system.

Turning first to FIG. 1, an exemplary hardware platform that can form one element of certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media, and may be internally installed in computer 102 or externally and removeably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object-oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

Figure 2:
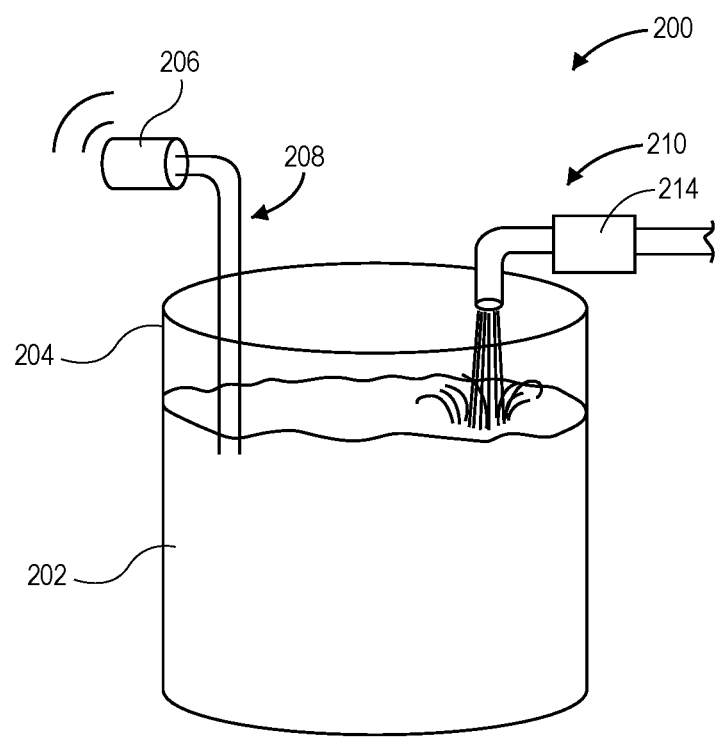
FIG. 2 depicts an exemplary scenario implementing embodiments of the invention.

FIG. 2 depicts an exemplary tank system 200 for detecting a conductive liquid 202. The conductive liquid 202 is disposed in a tank 204. In some embodiments, the tank 204 may be any receptacle containing moisture or liquid. In some embodiments, the conductive liquid 202 may be water, oil, gas, refrigerant, or any other liquid that may be conductive.

A sensor 206 may comprise electrodes 208. Further, the sensor 206 may include or be connected to processors, transmitters, and receivers. The processor may be or be connected to the computer 102 described above. The sensor 206 may be configured to detect when the liquid 202 contacts the electrodes 208. The electrodes 208 may be disposed in the tank 204 such that when the conductive liquid 202 reaches a level in the tank 204 the conductive liquid 202 is in contact with the electrodes 208. The sensor 206, in some embodiments, comprises a circuit for conducting a current, a microprocessor for detecting the circuit, and a power source for supplying the necessary power for the circuit. The sensor 206 is configured with components necessary to generate the a measurable electrical energy when the circuit is completed by the conductive liquid 202.

In some embodiments, a plurality of electrodes may be disposed in the conductive liquid 206. The processor may be, or may be in communication with, a controller. The controller may signal a valve 212 or plurality of valves to control the level of the conductive liquid 202 in the tank 204. For example, the tank system 200 may comprise a liquid input 210. The liquid input 210 may comprise the valve 212 that may be controlled by the processor of the sensor 206. The sensor 206 and the valve 212 may be in wired or wireless communication and may be connected through the local network 126 and the system bus 104 as described in the exemplary hardware platform in FIG. 1.

In some embodiments, there may be a plurality of electrodes connected to the circuit and processor. In some embodiments, there may be a plurality of sensors and electrodes in a single tank. In some embodiments, there may be a plurality of tanks that may be connected and a plurality of sensors detecting the liquid in the plurality of tanks. The level of the liquid in each tank may be controlled based on the levels in the other tanks. Any combination of tanks and sensors may be imagined in embodiments described herein.

Figure 3:
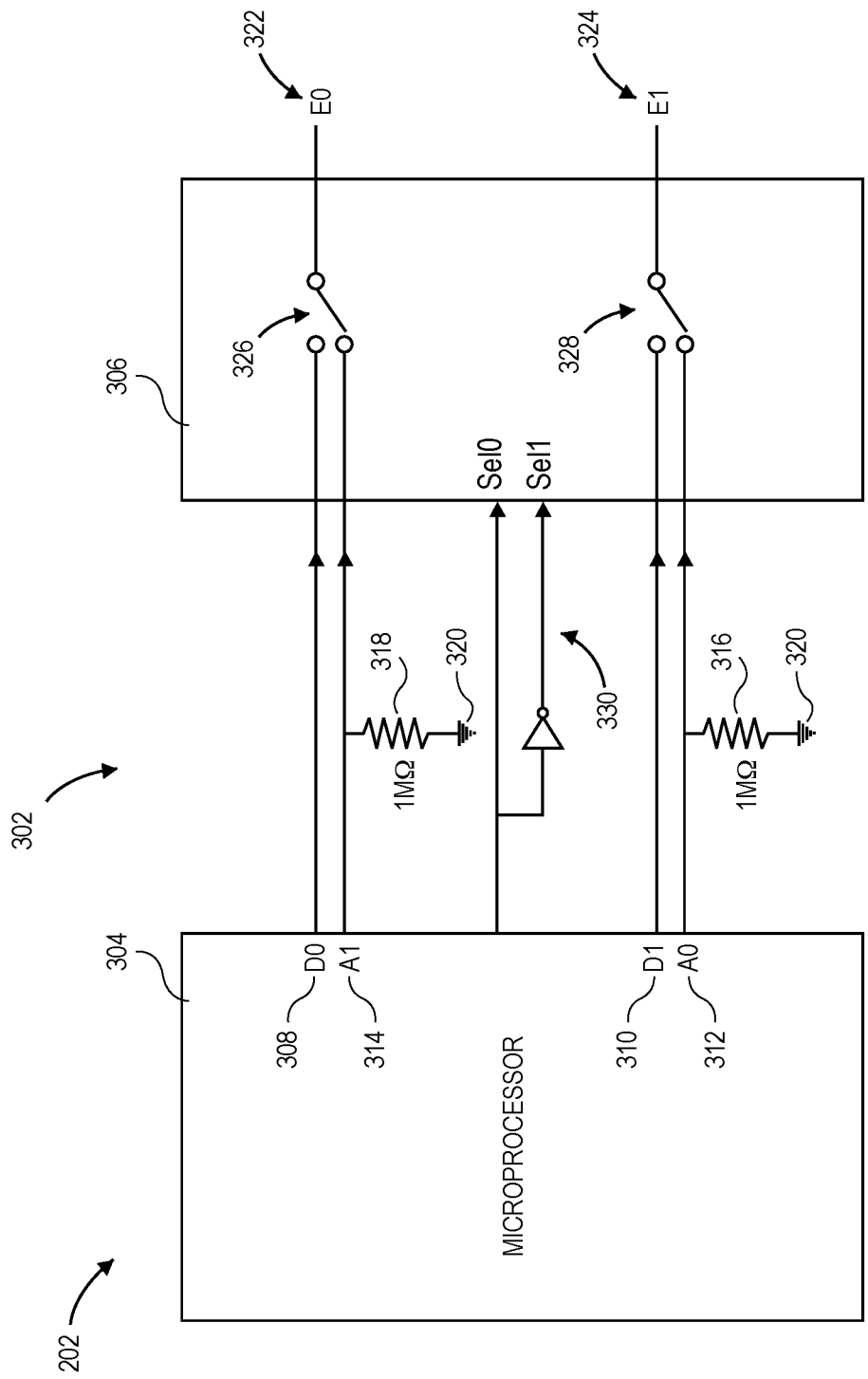
FIG. 3 depicts an embodiment of a circuit for detecting a conductive liquid.

FIG. 3 depicts an embodiment of the sensor 202. In some embodiments, the sensor 202 comprises a circuit 302 comprising a microprocessor 304 connected to a switching system 306. In some embodiments the microprocessor 304 comprises a first digital output 308, a second digital output 310, a first analog input 312 and a second analog input 314. In some embodiments, the circuit 304 further comprises a first resistor 316, a second resistor 318, a ground 320, a first electrode 322, and a second electrode 324. The first electrode 322 may be physically coupled to the first digital output 308 or the second analog input 318 by the first switch 326. The second electrode 324 may be physically coupled to the second digital output 310 or the first analog input 312 by the second switch 328. In some embodiments, the first switch 322 and the second switch 324 are Double Pole Single Throw (DPST) switches. The first electrode 322 and the second electrode 324 may be electrodes 208 described above. The first electrode 322 and the second electrode 324 may be separately disposed in the tank 204 for contacting the conductive liquid 202 in the tank 204 at a desired level as described above. When the first electrode 322 and the second electrode 324 contact the conductive liquid 202, the circuit 302 may be closed and thus, conduct electricity. Therefore, when a power is supplied to the circuit 302 and when the electrodes 208 contact the conductive liquid 202, a voltage may be measured at the microprocessor 304.

In some embodiments, the microprocessor 304 is the CPU 106, or the processor and controller described above. In some embodiments, the microprocessor 304 is communicatively connected to the CPU 106. The microprocessor 304 may comprise an ammeter and a voltmeter or any other sensor for detecting the electric power in the circuit 302. The microprocessor 304 may also supply the power from a power source such as a battery or a generator.

In some embodiments, the microprocessor 304 is connected to the switching system 306 comprising two DPST switches (i.e. the first switch 326 and the second switch 328). In a first configuration the first switch 326 is configured to connect the first digital output 308 to the first electrode 322. The second switch 324 is configured to connect the first analog input 312 to the second electrode 324. The first configuration is used in the first part and the second part of the four-part conductive liquid detection process.

During the first part of the four-part conductive liquid detection process, a digital high is applied at the first digital output 308. The circuit 302 is completed by conducting the electricity through the conductive liquid 202 in which the first electrode 322 and the second electrode 324 are submerged. A first voltage measurement is taken at the first analog input 312.

The second part of the four-part conductive liquid detection process comprises applying a digital low at the first digital output 308. A second voltage is measured at the first analog input 312. The first voltage may be subtracted from the second voltage, or vice versa, to cancel asymmetry effects and common-mode noise.

Regarding parts three and four, the circuit configuration is switched. The first switch 326 is configured to physically connect the second analog input 314 to the first electrode 322. The second switch 328 is configured to physically connect the second digital output 310 to the second electrode 324. The same process is carried out as described in parts one and two in the second configuration.

In some embodiments, in the second configuration, the circuit 302 is similar to the first configuration described above employing parts one and two. However, the current is flowing in the opposite direction between the first electrode 322 and the second electrode 324 in the second configuration. The digital high is provided at the second digital input 310. The second digital input 310 is physically connected to the second electrode 324 by the second switch 328. The second analog input 314 is connected to the first electrode 322 by the first switch 326. The first resistor 318 is disposed between the first switch 326, the second analog input 314, and ground 320. When the first electrode 322 and the second electrode 324 contact the conductive liquid 202, the circuit 302 is closed. Consequently, current flows from the second digital output 310 to the second analog input 314. A first voltage may be measured at the second analog input 314. Next, a digital low may be provided at the second digital output 310 and a second voltage may be measured at the second analog input 314. A difference between the first voltage and the second voltage may be determined. In some embodiments, the first voltage and the second voltage include common mode noise and asymmetry effects. Taking the difference of the first voltage and the second voltage cancels the asymmetry effects and common mode noise as described in reference to FIGS. 4A and 4B below.

The two configurations described above allow current to flow in opposite directions. In the first configuration, the current flows from the first electrode 322 to the second electrode 324. In the second configuration the current flows from the second electrode 324 to the first electrode 322. Consequently, the effects of electrolysis are negated. Any material build up that may occur as a result of the first configuration is undone during the process of the second configuration. Providing two alternating currents flowing in opposite directions reduces the effect of electrolysis and prolongs the life of the electrodes 208 and the circuit 302.

Figure 4A:
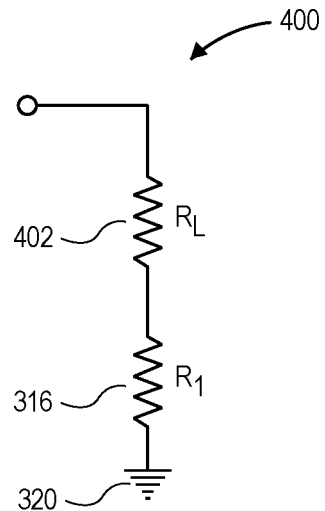
FIGS. 4A and 4B depict an embodiment of exemplary circuits representing asymmetry effects.
Figure 4B:
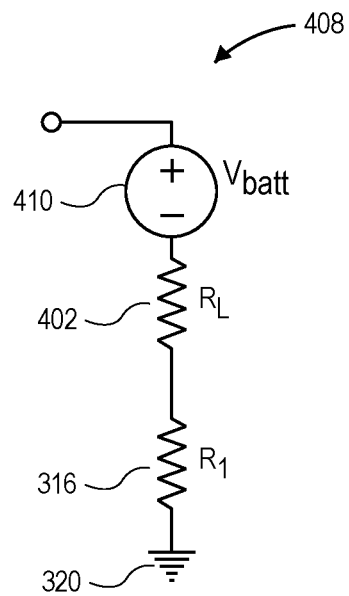

Turning to an embodiment of an exemplary circuit depicted in FIGS. 4A and 4B, when the first electrode 322 and the second electrode 324 contact the conducting liquid 202, the circuit 302 is closed. Consequently, a measurable voltage is applied at the microprocessor 304 between the first digital output 308 and the first analog input 312. The resulting circuit 302 comprises the power source supplied through the first digital output 308, the resistance of the conductive liquid 202, the first resistor 316, and the ground 320. The circuit 302 may be viewed as a voltage drop circuit.

FIG. 4A depicts an exemplary diagram of embodiments of the circuit 302 described above generally referenced by the numeral 400. The circuit diagram 400 is a representation of the two configurations of the circuit 302 described above. The circuit diagram 400 includes the liquid resistance 402, the first resistor 316, and the ground 320. As described, the circuit diagram 400 is representative of the first configuration with the digital high provided at the first digital output 308 and the return at the first analog input 312. This is exemplary and it is understood that the same process may be described for the second configuration as well.

When a five volt digital high is provided at the first digital input 308, the resistance of the conductive liquid 202 may be calculated using the following equation. In some embodiments, the first resistor 316 is 1 Mega-Ohms creating a high-impedance circuit 302.

$$R_L = \frac{1\ M\Omega(5\ V - V_{A_0})}{V_{A_1}} \qquad \text{(Eq. 1)}$$

This general equation is ideal and does not include asymmetry effects from the asymmetries in the electrodes. FIG. 4B depicts an exemplary diagram 408 of the circuit diagram 400 with asymmetry effects 410 included. Solving the above equation for the voltage measurement at the first analog input 312 ($A_1$) and including asymmetry effects results in the following equation.

$$V_{A_0} = \frac{1\ M\Omega(5\ V - V_{asym})}{R_{liquid} + 1\ M\Omega} \qquad \text{(Eq. 2)}$$

Further, with the switch in the same first configuration, providing a digital low at the first digital output 308 and taking the same measurement at the first analog input 312 results in the following equation.

$$V_{A_0} = \frac{1\ M\Omega(0\ V - V_{asym})}{R_{liquid} + 1\ M\Omega} \qquad \text{(Eq. 3)}$$

As can be seen, calculating a difference between equations 2 and 3 cancels the asymmetry effect voltage $V_{asym}$. Therefore, the asymmetry effects and common mode noise inherent in both measurements can be cancelled from the measurements using this method. A first final voltage may be determined by determining a difference between the first voltage measurement and the second voltage measurement in the circuit 302 first configuration. A second final voltage may be determined by applying the same process to the second configuration. When both the first final voltage and the second final voltage are found, a final voltage may be determined by averaging the first final voltage and the second final voltage. The final voltage may be indicative of the first electrode 322 and the second electrode 324 in contact with the conductive liquid 202. Further, the final voltage may be indicative of a resistance of the conductive liquid 202.

Figure 5:
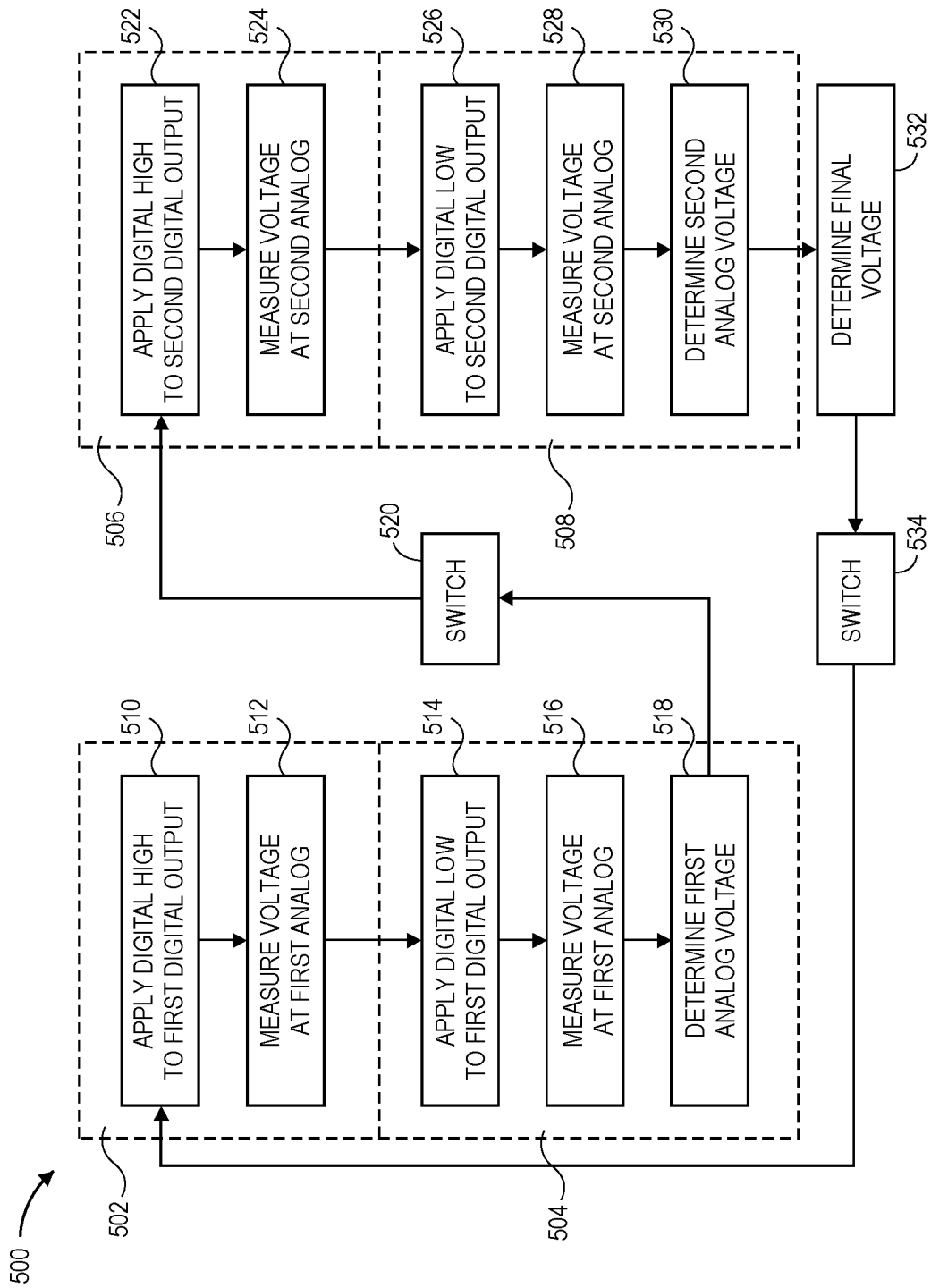
FIG. 5 depicts a flow diagram of a method of detecting a conductive liquid.

FIG. 5, depicts the exemplary four-part process for detecting the conductive liquid 202 generally referenced by the numeral 500. Part one 502 depicts a process with a digital high connected to the first digital output 308 and measuring the voltage at the first analog input 312. Part two 504 depicts a digital low connected to the first digital output 308 and measuring the voltage at the first analog input 312. Part two 504 further comprises determining the first final voltage with eliminated asymmetry effect as described in embodiments above. After part two 504, the output and inputs are switched. At part three 506, a digital high is applied at the second digital output 310 and a voltage measurement is taken at the second analog input 314. At part four 508, digital low is applied at the second digital output 310 and a voltage measurement is taken at the second analog input 314. The second final voltage with eliminated asymmetry effect is determined. The first final voltage and the second final voltages are averaged to determine the final voltage. The final voltage is indicative of an electrical connection between the first electrode 322 and the second electrode 326 where the electrical connection is made by the conductive liquid 202. Each part is discussed in more detail below.

At step 510 of part one 502, a digital high is applied to the first digital output 308. In some embodiments, the digital high is provided by the microprocessor 304 and is a five-volt output or in the range of four to six volts. Though a five-volt output is described in embodiments herein, any voltage may be applied.

At step 512 of part one 502, when the digital high is applied at the first digital output 308 a first voltage measurement is taken at the first analog input 312. In some embodiments, this creates a voltage divider circuit. The first voltage measurement may be indicative of the first electrode 322 and the second electrode 324 submerged in the conductive liquid 202. The first voltage measurement may also be indicative of the resistance of the conductive liquid 202. Further, if an analog to digital converter is applied before the first analog input 312, an extremely accurate measurement of the resistance of the conductive liquid 202 may be determined. At this stage, the first voltage measurement includes asymmetry effects and noise.

At step 514 of part two 504, a digital low is applied to the first digital output 308. The digital low provides a signal inverted relative to part one such that the asymmetry voltage may be subtracted out of the first voltage measurement determined in part one.

At step 516 of part two 504, a second voltage measurement is taken at the first analog input 312. The second voltage measurement is indicative of the resistance from the conductive liquid 202 and the resistor. Again, the second voltage measurement includes asymmetry effects and noise.

At step 518 of part two 504, the first voltage measurement and the second voltage measurement are compared to determine a first final voltage measurement without asymmetry effects and noise. In some embodiments, a difference between the first voltage and the second voltage is determined. This difference cancels the asymmetry effect that is present in both measurements. The difference cancels common-mode noise effects associated with the asymmetry.

At step 520, the circuit 302 configuration is switched from the first digital output 308 to the second digital output 310 and from the first analog input 312 to the second analog input 314. In some embodiments, the microprocessor 304 sends a signal to the switch 306 via a selection line 330 to actuate the first switch 326 and the second switch 328. The switching may occur at any frequency and as many times as necessary to obtain accurate measurements and voltage calculations. Further, the switching may be performed based on electrolysis and the condition of the first electrode 322 and the second electrode 324. In some embodiments, a resistance of the conductive liquid 202 also may be determined and the switch timing may be further determined by that process.

At step 522 of part three 506, a digital high is applied to the second digital output 310. In some embodiments, the digital high is provided by the microprocessor 304 and is a five-volt output as described in embodiments above.

At step 524 of part three 506, when the digital high is applied at the second digital output 310 a third voltage measurement is taken at the second analog input 314. The third voltage measurement may be indicative of the first electrode 322 and the second electrode 324 submerged in the conductive liquid 202. Further, the third voltage measurement includes asymmetry effects and noise.

At step 526 of part four 508, a digital low is apply to the second digital output 310. This digital low provides an inverted signal such that the asymmetry effects may be subtracted out of the voltage measurements.

At step 528, a fourth voltage measurement is taken at the second analog input 314. The fourth voltage measurement may include asymmetry effects and noise and is indicative of the first electrode 322 and the second electrode 324 being submerged in the conductive liquid 202.

At step 530 of part four 508, the third voltage measurement and the fourth voltage measurement of parts three and four are compared to determine a second final voltage measurement without asymmetry effects and common mode noise. The fourth voltage measurement may be subtracted from the third voltage measurement to determine the second final voltage or vice versa. At step 532, the first final voltage and the second final voltage are averaged to determine the final voltage. The final voltage may be indicative of the first electrode 322 and the second electrode 324 in contact with the conductive liquid 202.

At step 534, the circuit 302 is switched back to the first configuration. The process is then repeated starting at step 510 of the first part 502. The process is repeated alternating back and forth to reduce/eliminate electrolysis. This prolongs the life of the electrodes and the circuit 302 while filtering asymmetry effects and noise.

In some embodiments, a high-resolution analog-to-digital converter may be introduced into the circuit 302 after the current has passed between the electrodes 208. The analog signal may be converted into a digital signal for receipt and processing at a processor and determination of accurate liquid conductivity and resistance.

The insulating components and methods of use of the circuits and the components comprising the circuits provided herein may be used individually or in any combination. It should be appreciated that, while the above disclosure has been generally directed to the field of detecting a conductive liquid in tanks, the conductive liquid detection system could be used in any liquid vessel and environment.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A method of detecting a conductive liquid with electrodes of a circuit disposed in the conductive liquid, the method comprising the steps of:

applying a first digital high at a first digital output of a microprocessor;

wherein the first digital high is connected to a first electrode by a first switch;
measuring a first voltage at a first analog input of the microprocessor,
wherein the first analog input is connected to a second electrode by a second switch;
applying a first digital low at the first digital output;
measuring a second voltage at the first analog input;
determining a first final voltage by calculating a difference between the first voltage and the second voltage;
switching the first switch to connect a second analog input to the first electrode;
switching the second switch to connect a second digital output to the second electrode;
applying a second digital high at the second digital output;
measuring a third voltage at the second analog input;
applying a second digital low at the second digital output;
measuring a fourth voltage at the second analog input;
determining a second final voltage by calculating a difference between the third voltage measurement and the fourth voltage measurement; and
determining a final voltage by averaging the first final voltage and the second final voltage,
wherein the final voltage is indicative of the first electrode and the second electrode contacting the conductive liquid.

2. The method of claim 1,
wherein the first digital high and the second digital high have a signal strength of between four volts and six volts, and
wherein the first digital low has a signal strength between zero volts and one volt.

3. The method of claim 1,
wherein the first switch and the second switch are double pole single throw switches, and
wherein a signal to switch is received from the microprocessor.

4. The method of claim 1,
wherein the final voltage is further indicative of a resistance from at least one resistor, and
wherein the at least one resistor has a resistance of one Mega-Ohm.

5. The method of claim 1,
wherein the calculation of the first final voltage eliminates asymmetry effect from the first final voltage, and
wherein the calculation of the second final voltage eliminates asymmetry effect from the second final voltage.

6. The method of claim 1, wherein a frequency of switching the first switch and the second switch is based at least in part on an electrolysis between the first electrode and the second electrode.

7. The method of claim 1, further comprising the step of determining the resistance of the conductive liquid, wherein an analog to digital converter converts an input from analog to digital.

8. The method of claim 7, further comprising the step of sending a signal from the processor to a valve for controlling a level of the conductive liquid, wherein the control of the valve is based at least in part on the final voltage.

9. The method of claim 1, further comprising the step of filtering a first input at the first analog input and a second input at the second analog input with a low pass filter to reduce noise.

10. The method of claim 1, further configured with a plurality of electrodes physically connected to the microprocessor by a plurality of switches.

11. A system of detecting a conductive liquid using electrodes in contact with the conductive liquid comprising:
a circuit for transmitting electrical signals between a output and an input, the circuit comprising:
a first electrode and a second electrode separately disposed in the conductive liquid; and
a microprocessor including a digital output selectively attached to the first electrode and an analog input selectively attached to the second electrode,
wherein a digital high is applied at the first digital output,
wherein a digital low is applied at the first digital output; and
one or more non-transitory computer-readable media storing computer-executable instructions that, when executed by a processor, perform a method of detecting the conductive liquid, the method comprising the steps of:
measuring a first voltage at the analog input when the digital high is applied at the digital output;
measuring a second voltage at the analog input when the digital low is applied at the digital output;
determining a first final voltage by calculating a difference between the first voltage and the second voltage,
wherein the first final voltage is indicative of the first electrode and the second electrode in contact with the conductive liquid.

12. The system of claim 11,
wherein the digital output is a first digital output and the analog input is a first analog input; and
further comprising a second digital output selectively attached to the second electrode and a second analog input selectively attached to the first electrode,
wherein the digital high is applied at the second digital output;
wherein the digital low is applied at the second digital output; and
wherein the media is further executable to perform the steps of:
measuring a third voltage at the second analog input when the digital high is applied at the second digital input;
measuring a fourth voltage at the second analog input when the digital low is applied at the second digital input;
determining a second final voltage by calculating a difference between the third voltage and the fourth voltage; and
determining a final voltage by averaging the first final voltage and the second final voltage.

13. The system of claim 12,
wherein the digital high has a signal strength of between four volts and six volts,
wherein the conductive liquid is water,
wherein the first electrode is switched from the first digital output to the second analog input by a double pole single throw switch, and
wherein a signal to switch is sent by the microprocessor.

14. The system of claim 11, wherein the media is further executable to perform the step of subtracting the first final voltage from the second final voltage to eliminate asymmetry effects and common-mode noise.

15. The system of claim 11, further comprising a valve for controlling a level of the conductive liquid,
wherein the valve is actuated by a signal sent by the processor, and wherein the control of the valve is based at least in part on the final voltage.

16. The system of claim 11, further comprising an analog to digital converter,
   wherein the analog to digital converter converts an input from analog to digital, and
   wherein the media is further executable to determine a resistance of the conductive liquid from the digital input.

17. A method of detecting a conductive liquid with electrodes of a circuit disposed in the conductive liquid, the method comprising the steps of:
   applying a first electrical power at a first digital output connected to a first electrode by a first switch;
   measuring a first voltage at a first analog input connected to a second electrode by a second switch;
   applying a second electrical power at the first digital output;
   measuring a second voltage at the first analog input;
   applying the first electrical power at a second digital output connected to the second electrode by the second switch;
   measuring a third voltage at a second analog input connected to the first electrode by the first switch;
   applying the second electrical power at the second digital output;
   measuring a fourth voltage at the second analog input;
   determining a first final voltage by calculating a difference between the first voltage and the second voltage,
   wherein calculating the difference between the first voltage and the second voltage cancels a first asymmetry effect between the first electrode and the second electrode;
   determining a second final voltage by calculating a difference between the third voltage and the fourth voltage,
   wherein calculating the difference between the third voltage and the fourth voltage cancels a second asymmetry effect between the first electrode and the second electrode; and
   determining a final voltage by averaging the first final voltage and the second final voltage.

18. The method of claim 17,
   wherein the first electrical power is a digital high between four volts and six volts, and
   wherein the second electrical power is a digital low between zero volts and one volt.

19. The method of claim 17,
   wherein the first switch and the second switch are double pole single throw switches, and
   wherein a signal to actuate the switches is sent by the microprocessor.

20. The method of claim 19, wherein a frequency of switching is based at least in part on an electrolysis between the first electrode and the second electrode.

* * * * *